United States Patent [19]
Martin

[11] Patent Number: 5,112,969
[45] Date of Patent: May 12, 1992

[54] CYANO ESTERS AND AZEPINONES

[75] Inventor: Daniel E. Martin, Lee's Summit, Mo.

[73] Assignee: Merrell Dow Pharmaceuticals Inc., Cincinnati, Ohio

[21] Appl. No.: 707,486

[22] Filed: May 30, 1991

Related U.S. Application Data

[60] Continuation-in-part of Ser. No. 502,619, Apr. 2, 1990, which is a division of Ser. No. 440,377, Nov. 22, 1989, which is a continuation-in-part of Ser. No. 400,658, Aug. 31, 1989.

[51] Int. Cl.$^5$ .......................................... C07D 281/10
[52] U.S. Cl. ................................................... 540/491
[58] Field of Search ......................................... 540/491

[56] References Cited

U.S. PATENT DOCUMENTS

| | | | |
|---|---|---|---|
| 3,401,166 | 9/1968 | Krapcho | 540/491 |
| 3,562,257 | 2/1971 | Kugita et al. | 540/491 |
| 4,552,695 | 11/1985 | Igarashi et al. | 540/491 |
| 4,567,175 | 1/1986 | Takeda et al. | 514/211 |
| 4,808,580 | 2/1989 | Mohacsi et al. | 514/211 |
| 4,902,684 | 2/1990 | Floyd et al. | 540/491 |

OTHER PUBLICATIONS

Kugita et al., Synthesis of 1,5-Benzpthiazepine Derivatives, I, Chem. Pharm. Bull., 18 (10), pp. 2028-2037 (1970).

Kugita et al., A Mild and Selective Method of Ester Hydrolysis, Synth. Commun., 19 (3 & 4), pp. 627-631 (1989).

Kohler et al., J. Am. Chem. Soc., 49, pp. 3181-3188 (1927), "An Apparatus for Determining both the Quantity of Gas Evolved and the Amount of Reagent Consumed in Reactions with Methyl Magnesium Iodide".

Primary Examiner—C. Warren Ivy
Assistant Examiner—Celia Chang
Attorney, Agent, or Firm—Stephen L. Nesbitt

[57] ABSTRACT

A cyano glycidic acid ester compound can be prepared by reaction of an alkyl haloester and a cyano-aldehyde in the presence of an alkali metal alkoxide; an amino-acid ester cyano compound can be prepared by reaction of the cyano glycidic acid ester compound and an attachable amino compound, and a cyclic amido-carbonyl cyano compound can be prepared by contact of the amino-acid ester cyano compound in a liquid medium with a heterogeneous acidic ion-exchange substance. For example, reaction of 4-cyanobenzaldehyde and methyl chloroacetate in the presence of sodium methoxide in methanol, followed by ice/acetic acid neutralization, prepares trans-3-(4-cyanophenyl)glycidic acid, methyl ester, which is reacted in toluene with 2-aminothiophenol to yield 2-hydroxy-3-(2-aminophenylthio)-3-(4-cyanophenyl)propionic acid, methyl ester, threo form, which is cyclized in an aqueous mixture into cis-2-(4-cyanophenyl)-3-hydroxy-2,3-dihydro-1,5-benzothiazepin-4(5H)-one by employing a sulfonated polystyrenedivinylbenzene ion-exchange resin in its acid form, e.g., Dowex 50X4-400, at cyclization yields exceeding 70 percent of theory. Compounds of this invention are useful pharmaceuticals.

4 Claims, No Drawings

CYANO ESTERS AND AZEPINONES

This is a continuation-in-part of U.S. Ser. No. 07/502,619, filed Apr. 2, 1990, which is a divisional of U.S. Ser. No. 07/440,377, filed Nov. 22, 1989, which is a continuation-in-part of U.S. Ser. No. 07/400,658, filed Aug. 31, 1989.

This invention concerns organic reactions, and organic cyclization reactions employing ion-exchange substances, useful for preparing organic cyano compounds, and, for example, benzothiazepine pharmaceuticals, and these compounds and intermediates thereto as well.

BACKGROUND

Various benzothiazepines, useful intermediates or pharmaceuticals, and procedures to prepare them, are known. See e.g., Krapcho, U.S. Pat. No. 3,410,166 (Sept. 10, 1968); Kugita et al., U.S. Pat. No. 3,562,257 (Feb. 9, 1971); Igarashi et al., U.S. Pat. No. 4,552,695 (Nov. 12, 1985); Kugita et al., Chem. Pharm. Bull., 18(10), 2028–37 (1970); Takeda et al., U.S. Pat. No. 4,567,175 (Jan. 28, 1986); Mohacsi et al., U.S. Pat. No. 4,808,580 (Feb. 28, 1989); Floyd et al., U.S. Pat. No. 4,902,684 (Feb. 20, 1990).

Basu et al., Synth. Commun. 19(3 and $), 627–31 (1989), reports on a mild and selective method of ester hydrolysis. This method employs Dowex-50 resin.

Further benzothiazepines, e.g., cyano-containing-3-oxybenzothiazepines, and so forth, and procedures to prepare them, are lacking. Such would be highly significant and are needed. The otherwise reactable cyano moiety on such a product may be viewed as an obstacle to its provision.

SUMMARY

This invention provides, in material aspects, 1) a cyano glycidic acid ester compound, 2) an amino-acid ester cyano compound, and 3) a cyclic amido-carbonyl cyano compound. Procedural aspects include 1) a procedure for preparing a cyano glycidic acid ester compound comprising contacting a haloalkyl ester and a cyano-aldehyde in the presence of an alkali metal base under conditions sufficient to prepare the cyano glycidic acid ester compound, 2) a procedure for preparing an amino-acid ester cyano compound comprising contacting a cyano glycidic acid ester compound with an attachable amino a compound under conditions sufficient to prepare the amino-acid ester cyano compound, and 3) a procedure for cyclization of an amino-acid ester cyano compound comprising contacting the amino-acid ester cyano compound in a liquid medium with a heterogeneous acidic ion-exchange substance under conditions sufficient to form a cyclic amido-carbonyl cyano compound.

This invention provides useful chemical intermediates to chemicals to include pharmaceuticals. With respect to the cyclic amido-carbonyl compounds, these compounds in general are intermediates to or are useful as antidepressants, tranquilizers, and coronary vasodilators.

In addition, certain of the cyclic amido-carbonyl compounds, e.g., cis-2-(4-cyanophenyl)-2,3-dihydro-3-hydroxy-4-[2-(piperidino)ethyl]-1,5-benzothiazepin-4(5H) -one, hydrochloride (salt, significantly, can provide effective activity as an ameliorator of a generalized tonic-clonic type epileptic seizure in a mammal, and moreover, can provide excellent activity as an anti-cancer drug potentiator. See, Zobrist et al., U.S. Pat. No. 4,963,545 entitled "BENZOTHIAZEPINE ANTI-SEIZURE METHOD," filed Nov. 22, 1989, and Ahmed, U.S. Pat. appl. Ser. No. 07/441,083 entitled, "ANTI-CANCER DRUG POTENTIATORS," filed Nov. 22, 1989, both of which are incorporated herein by reference.

Procedural embodiments of this invention, particularly in cyclizations, are characterizable in being highly efficient. In fact, they may be considered to be unexpectedly efficient in the yields which can be obtained thereby and surprisingly well-adapted to commercial production. Yields can be high and may be considered to be surprisingly so. Further, the practice of the invention, particularly in cyclizations, does not generally require expensive reagents or solvents, or chemicals presently known to be highly dangerous in general, and it can be carried out safely in general on an industrial scale. The ion-exchange substance may be regenerated and recycled for further use. Moreover, that particular aspect of the invention is adapted to cyclization reactions where the otherwise reactable cyano moiety, not desired to be reacted, is generally not reacted in a side reaction to the cyclization reaction.

Further advantages attend the invention as well.

ILLUSTRATIVE DETAIL

Herein, the term "cyano glycidic acid ester compound" refers to an organic chemical compound which contains an epoxy ring functionality, with an organic ester functionality of an acid being bonded to an epoxy carbon, and with an organic moiety, having cyano functionality, being bonded to an epoxy carbon. Desirably, the compound has one epoxy ring functionality per molecule; the ester functionality is bonded to one epoxy carbon of the epoxy ring functionality and is an ester of a carboxylic acid, and the organic moiety, having cyano functionality, is bonded to the other epoxy carbon of the epoxy ring functionality and is aromatic with a cyano moiety being attached to the aromatic nucleus. The aromatic nucleus is preferably a phenyl ring. The ester is advantageously an alkyl ester, especially a lower alkyl ester, to include, of course, propyl, ethyl and methyl esters. The methyl ester is the preferred ester in the present invention.

Preferably, the cyano glycidic acid ester compound is represented by a compound of the following general formula:

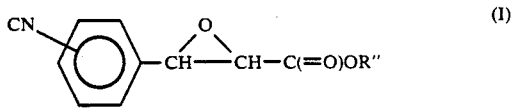
(I)

wherein R" is alkyl.

Of the compounds represented by the formula (I), the following are especially noted as being those wherein the specifically-noted cyano (CN) moiety is para-positioned, and R" is lower alkyl, but preferably methyl.

Of note, the cyano glycidic acid ester compound may be optically inactive or optically active. Such isomers as the cis and trans isomers, for example, may be isolated.

Herein, the term "amino-acid ester cyano compound" refers to an organic chemical compound which contains an amino functionality generally having at least one active hydrogen atom therein as determined by the Zerewitinoff test, see generally, Kohler et al., *J. Am. Chem. Soc.*, 49, 3181-88 (1927), which contains an organic ester functionality of an acid, and which contains an organic moiety, having cyano functionality. The amiho-acid ester cyano compound is generally such that it will generally cyclize, preferably internally, during the procedure of the invention. Desirably, the amino functionality has two active hydrogen atoms therein as determined by the Zerewitinoff test; the ester functionality is an ester of a carboxylic acid; the amino functionality and the carbonyl carbon of the carboxylic acid ester are separated by from three to six other atoms as in a backbone of the compound, and the organic moiety, having cyano functionality, is aromatic with a cyano moiety being attached to the aromatic nucleus. The aromatic nucleus is preferably a phenyl ring. Again, the ester is advantageously an alkyl ester, especially a lower alkyl ester, to include, of course, propyl, ethyl and methyl esters, and the methyl ester is the preferred ester.

Preferably, the amino-acid ester cyano compound is represented by a compound of the following general formula:

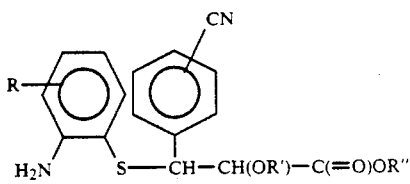

(II)

wherein
R is a generally inert moiety;
R' is a generally inert moiety, and
R" is alkyl.

The term "generally inert" refers herein to hydrogen and other moieties which do not generally interfere with the procedural practice of this invention.

Of the compounds represented by the formula (II), the following are especially noted as being those wherein
R is H, or Cl, to include those having the Cl para to the required amino moiety of the aromatic ring, but preferably H;
the specifically-noted CN moiety is para-positioned;
R' is H or acetyl, but preferably H, and
R" is lower alkyl, but preferably methyl.

Of note, the amino-acid ester cyano compound may be optically inactive or optically active. Such isomers as the threo and erythryo isomers may be isolated.

Herein, the term "cyclic amido-carbonyl cyano compound" refers to a cyclic amido-carbonyl compound having cyano functionality, which is an organic compound which is heterocyclic, as a minimum, generally due to an amido nitrogen, formerly of the amino-acid ester cyano compound, being coupled to a carbonyl carbon, also formerly of the amino-acid ester cyano compound, therein, and which contains an organic moiety, having cyano functionality. Desirably, the organic moiety, having cyano functionality, is aromatic with a cyano moiety being attached to the aromatic nucleus, which is not fused to the heterocyclic ring having the amido nitrogen and the carbonyl carbon but is instead bonded through a single carbon of the aromatic nucleus; the heterocyclic amido nitrogen bears one active hydrogen as determined by the Zerewitinoff test, and the required heterocyclic feature of the cyclic amido-carbonyl cyano compound is embodied in a five to eight atom ring. It is further desired to have another hetero atom, especially for example, a sulfur atom, in this formed ring. The aromatic nucleus is preferably a phenyl ring.

Preferably, the cyclic amido-carbonyl cyano compound is a cyano 1,5-benzothiazepine, and especially a cyano 1,5-benzothiazepine represented by a compound, or suitable salt thereof, of the following general formula:

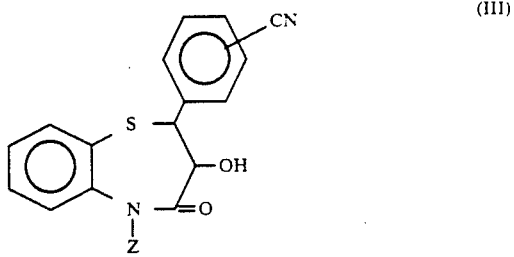

(III)

wherein Z is 2-(N-piperidino)ethyl.

The salt may be a suitable pharmaceutically acceptable salt. Pharmaceutically acceptable salts include the hydrochloride, fumarate, maleate, citrate and sulfate salts, and so forth.

Especially noted cyclic amido-carbonyl cyano compounds thus particularly include those of the formula (III) wherein the specifically-noted CN moiety is para-positioned.

Herein, a procedure is a method and/or process.

Herein, the term "haloalkyl ester" refers to a compound having an organic ester functionality of an acid, and also, bonded to the carbonyl carbon thereof, a haloalkyl group. Desirably, the ester is an ester of a carboxylic acid and the haloalkyl group is a halomethyl group. Again, the ester is advantageously an alkyl ester, especially a lower alkyl ester, to include, of course, propyl, ethyl and methyl esters, and the methyl ester is the preferred ester.

Preferably, the haloalkyl ester is represented by a compound of the following general formula:

$$XCH_2-C(=O)OR''$$ (Ia)

wherein
X is halogen, to include F, Cl, Br and I, especially Cl or Br, but preferably Cl, and
R" is alkyl, especially lower alkyl, but preferably methyl.

The preferred species of haloalkyl ester is methyl chloroacetate.

Herein, the term "cyano-aldehyde" refers to a compound which contains an organic moiety, having cyano functionality, and an aldehyde functionality. Desirably, the organic moiety, having cyano functionality, is aromatic with a cyano moiety being attached to the aromatic nucleus, and the aldehyde functionality is attached to the same aromatic nucleus. The aromatic nucleus is preferably a phenyl ring.

Preferably, the cyano-aldehyde is represented by a compound of the following general formula:

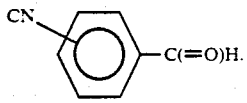

(Ib)

Of the compounds represented by the formula (Ib), the especially noted compound is that wherein the specifically-noted cyano (CN) moiety is para-positioned, which is 4-cyanobenzaldehyde.

Herein, the term "alkali metal base" refers to a base of an alkali metal. Desirably, the alkali metal base is present in a liquid diluent, especially, as may be appropriate, such as in an ether, e.g., tetrahydrofuran, or an alkyl alcohol, e.g., methanol.

Preferably, the alkali metal base is an alkali metal hydride or an alkali metal alkoxide, as is represented by compounds of the following general formula:

MH or R'''OM  (Ic)

wherein
H is hydride;
M is the residue or cation of an alkali metal to especially include residues or cations of Na or K, and
R''' is alkyl, especially lower alkyl to include such as, for example, methyl, ethyl, t-butyl, and so forth.

The preferred species of alkali metal base is sodium methoxide, especially as present in methanol.

Herein, the term "attachable amino compound" refers to an organic compound bearing amino functionality generally having at least one active hydrogen atom therein as determined by the Zerewitinoff test, the compound being able to be attached to the cyano glycidic acid ester compound in procedural practice of this invention by chemical reaction with the epoxy functionality of the cyano glycidic acid ester compound. The organic residue of the attachable amino compound advantageously is aromatic, the aromatic nucleus bearing the amino functionality. The aromatic nucleus is preferably a phenyl ring. Desirably, the amino functionality has two active hydrogen atoms therein as determined by the Zerewitinoff test. It is also desired to have another hetero atom functionality, for example, thiol functionality, attached to the organic residue bearing the amino functionality, which can react with the epoxy ring of the cyano glycidic acid ester compound to form the amino-acid ester cyano compound.

Preferably, the attachable amino compound is represented by a compound of the following general formula:

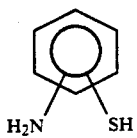

(IIa)

Of the compounds represented by the formula (IIa), the following are especially noted as being those wherein the specifically-noted primary amino (NH$_2$) moiety is ortho to the especially-noted thiol (SH) moiety. The preferred species of the attachable amino compound is 2-aminothiophenol.

Herein, the term "liquid medium" refers to a substance which is substantially liquid during the procedure of the invention. Typically, the liquid medium functions as a minimum as a diluent in the practice of this invention. The liquid medium employed in cyclization in this invention is typically a hydroxylated compound such as water and/or alcohol(s), with an aqueous diluent being preferred at that stage. More than one substance or diluent may be employed, as appropriate.

Herein, the term "heterogeneous acidic ion-exchange substance" refers to a substance which is generally considered a solid and which has acid functionality suitable for carrying out the practice of this invention bonded therewith. Thus, the heterogeneous acidic ion-exchange substance can be of a synthetic polymer matrix, i.e., resin, with appropriate acidic functionalities bonded thereto, and may also include other types of exchange substances typically or high capacity acidic functionality such as appropriate inorganic ion-exchange crystals and exchange materials made by introducing appropriate acidic functional groups into polyacrylamide gels, celluloses, or dextrans, and so forth and the like. Preferably however, the heterogeneous acidic ion-exchange substance is an acidic ion-exchange resin, especially of the strong acid type, to include a strong acid phenolic type such as, for example, a sulfonated phenolic type ion-exchange resin in its acid form, e.g., Bio Rex ®40, etc., but particularly one such as, for example, a so-called sulfonated polystyrenetype ion-exchange resin, to include a polystyrenedivinylbenzene ion-exchange resin, in its acid form. Examples of commercially available sulfonated polystyrenedivinylbenzene ion-exchange resins include Amberlite ® IR -120, Dowex-50 ®, Duolite C-20 TM, Ionac CGC-240 ®, Lewatit S -100, Permutit Q ®, Rexyn 101 ®, and Zeocarb 225 TM.

The heterogeneous acidic ion-exchange substance can be embodied in may forms. Beads are one example of this. Also, it can be advantageous to embody the heterogeneous acidic ion-exchange substance in a form such as a coating over a substantial area of a reaction vessel or chamber, or as a large plate or plates therein. Such embodiments as these more substantial latter-mentioned forms can provide, for example, a macro-solid form, from which cyclized organic compound may precipitate, and which thus can be used to advantage in separation of such precipitates from the remainder of any liquid reaction system found in the practice of this invention.

In general, the procedural aspects of the present invention can be carried out under batch-type processing conditions. Flow-type processing conditions can be employed as appropriate by those of skill in the art as well.

In the practice of this invention in its procedural aspect for preparing the cyano glycidic acid ester compound, the haloalkyl ester is contacted with the cyanoaldehyde in the presence of the alkali metal base. This procedural aspect of the present invention is carried out under conditions which are sufficient to prepare the cyano glycidic acid ester compound.

Of note, again, the cyano glycidic acid ester compound may be optically inactive or optically active. The trans isomer is desirably prepared and/or isolated.

A suitable diluent can be employed. Desirably, this diluent is an alkyl alcohol from in which, and from which, the alkali metal hydroxide resides, and is prepared.

Typically, the alkali metal base is obtained or prepared, for example, from the addition of sodium metal to excess methanol, and separately, the haloalkyl ester and the cyano aldehyde are mixed. Then, the mixture of the haloalkyl ester and the cyano aldehyde is contacted with the alkali metal base, for example, the alkali metal alkoxide in the alcoholic diluent. The haloalkyl ester and the cyano-aldehyde can be diluted before their mixing, before their contact with the alkali metal base.

Concentrations of diluted components can be any which are suitable for the purpose. Advantageously, concentrations of the diluted components, as employed for contact in the practice of this invention, are as follows:

Haloalkyl ester: About from neat onward, especially neat. Cyano-aldehyde: About from 0.1 to 6M, especially about from 1 to 3M.

Alkali metal base: About from 0.1 to 10M, especially about from 2 to 4M.

Temperatures for the contact are desirably low to moderate, to include those about from −40 to 50 degrees C., especially those about from -10 to 10 or to 30 degrees C. Initial contact is preferably carried out at lower ranges, but preferably about from −10 to 10 degrees C. Thereafter, the temperature may be kept as initially; the temperature may even be raised therefrom.

In general, agitation such as, for example, by stirring, is carried out throughout the contact, from which reaction into the cyano glycidic acid ester compound ensues.

Times for the contact as in batch processing can vary. Typical times include those about from several minutes to several days, especially those about from half of an hour to ten hours.

The reaction may be quenched by contact with an ice/acid mixture. For example, quenching can be accomplished by pouring the reaction mixture over ice followed by the addition of acetic acid, with stirring.

Product cyano glycidic acid ester compound can be collected by known methods. For example, the product may be a solid, with its collection by filtration.

The cyano glycidic acid ester compound may be purified if desired. For example, it may be purified by recrystallization techniques.

Yields of the cyano glycidic acid ester compound can be quite good, if not relatively excellent. Yields at least about 35, even at least about 45 or even at least about 50 percent of theory, after purifications, can be obtained.

In the practice of this invention in its procedural aspect for preparing the amino-acid ester cyano compound, the cyano glycidic acid ester compound is contacted with the attachable amino compound. This procedural aspect of the present invention is carried out under conditions which sufficient to prepare the amino-acid ester cyano compound.

A suitable diluent can be employed. Desirably, this diluent is an inert organic diluent, to include hydrocarbon liquids, especially for example, an aromatic hydrocarbon liquid, e.g., toluene.

Typically, the cyano glycidic acid ester compound is contacted with the attachable amino compound, for example, in the diluent. Either of the cyano glycidic acid ester compound or the attachable amino compound, or both, can be diluted before contact with the other. For example, the cyano glycidic acid ester compound can be thus pre-diluted with an aromatic hydrocarbon diluent, and then the attachable amino compound can be added neat thereto.

Concentrations of diluted components can be any which are suitable for the purpose. Advantageously, concentrations of the diluted components as in reacting mixture, i.e., when these required two compounds are in contact are as follows:

Cyano glycidic acid ester compound:
About from 0.01 to 5M, especially about from 0.1 to 2M.

Attachable amino compound:
About from neat onward, especially neat.

Temperatures for the contact are desirably moderate to moderately high, to include those about from 0° to 150° C., especially those about from 20° to 130° C. or so. Initial contact is preferably carried out at lower ranges, but advantageously about room temperature. Thereafter, the temperature can be raised therefrom, for example, to reflux temperatures of diluent employed.

In general, agitation such as, for example, by stirring, is carried out throughout the contact, from which reaction into the amino-acid ester cyano compound ensues.

Times for the contact as in batch processing can vary. Typical times include those about from several minutes to several days, especially those about from an hour to a score, i.e., twenty, hours.

Product amino-acid ester cyano compound can be collected by known methods. For example, the product may be a solid, with its collection by filtration, or the product may be in an oil, which may be purified into solid form by crystallization techniques.

The amino-acid ester cyano compound may be purified if desired. For example, it may be purified by recrystallization techniques.

Yields of the cyano glycidic acid ester compound can be quite good, if not relatively excellent. Yields at least about 35, even at least about 45 or even at least about 50 percent of theory, after purifications, can be obtained by the practice of this invention, based on the limiting amounts of the cyano glycidic acid ester compound or the attachable amino compound.

In the practice of this invention in its cyclizing procedural aspect, the amino-acid ester cyano compound is contacted in the liquid medium with the heterogeneous acidic ion-exchange substance. In general, cyclization of the amino-acid ester cyano compound takes place. This procedural aspect of the present invention is carried out under conditions which are sufficient to prepare the cyclic amido-carbonyl cyano compound.

The cyclization procedural aspect of the invention can be employed with all types of isomers of the amino-acid ester cyano compound, to include, for example, threo and erythro amino-acid ester cyano compounds of the formula (II), which cyclize to form cis and trans cyclic amidocarbonyl cyano compounds of the formula (III), respectively. It may well be advantageous to employ an appropriate optically enriched or optically pure amino-acid ester cyano compound sample in the practice of the present invention, especially in procedures which lead up to cyclic amido-carbonyl cyano compounds which are employed as intermediates to make optically active final products.

Of particular note, the amino-acid ester cyano compound sample employed should be of a suitable purity in the procedural practice of this invention. If the amino-acid ester cyano compound sample is not of a suitable purity, the procedure of this invention may result in undesirably low, or possibly no appreciable, yields. Other factors which may affect yields include reaction times, levels of agitation, and/or reaction vessel size.

The cyclization procedure of this invention is a heterogeneous phase procedure. It employs the generally solid heterogeneous acidic ion-exchange substance in the liquid medium to prepare the cyclic amido-carbonyl cyano compound.

Generally speaking, although the liquid medium may itself be composed of, say, the amino-acid ester cyano compound, i.e., the reaction may be run essentially neat with respect to the amino-acid ester cyano compound, the liquid medium is typically provided by a substance other than the amino-acid ester cyano compound itself and which is substantially liquid during the procedure of the invention. Water is the preferred liquid medium.

Concentrations of the amino-acid ester cyano compound in relation to the liquid medium employed can vary widely. However, initial concentrations of the amino-acid ester cyano compound in the liquid medium, especially in relation to batch-type processing, more typically reside within concentrations about from 0.01 molar (M) to saturation levels, or even higher such as found in slurries, to generally include concentrations about from 0.05 to 1M and about from 0.1 to 0.6M. Preferably however, the amino-acid ester cyano compound is essentially dissolved into the liquid medium in the cyclization practice of this invention.

The heterogeneous acidic ion-exchange substance is typically used in its acidic, i.e., hydrogen ion, form. Generally, the ion-exchange substance may be regenerated and recycled for further use.

Amounts of the heterogeneous acidic ion-exchange substance which are employed in the cyclization practice of this invention are in general any which effect preparation of the cyclic amido-carbonyl cyano compound. A suitable amount of acid functionality will thus reside on the ion-exchange substance employed.

Temperatures employed in carrying out the cyclization procedure of the present invention are generally any which suffice to prepare the cyclic amido-carbonyl cyano compound. However, temperatures about from 50° to 150° C. are more typically employed, to generally include those about from 80° to 120° C. Reflux conditions can advantageously be employed, particularly when employing aqueous liquid media. Notably, the temperatures employed in carrying out the procedure of this invention thus can be fairly moderate.

Agitation of the amino-acid ester cyano compound in the liquid medium is typically employed. This helps bring about more efficient contact in the practice of the invention.

Duration of the contact or the time required to bring about the preparation of the cyclic amido-carbonyl cyano compound is generally that time required which brings about the desired level of completion in the cyclization procedure of the invention. In batch-type processing, such a time includes times about from several minutes to several days or more. More typically, the time employed in cyclizations in the practice of this invention ranges about from an hour or two to two or so days.

Prepared cyclic amido-carbonyl cyano compound may be employed in further processing such as in reactions as a chemical intermediate without its separation from the remaining components employed to make it, or it may be collected and separated from the remaining components employed to make it, as desired. Known methods can be employed.

For example, the prepared cyclic amido-carbonyl cyano compound can be generally insoluble in the liquid medium employed. In this case, the cyclic amido-carbonyl cyano compound can be collected directly by scooping, decanting, straining or filtering, which can be particularly advantageous when the acidic ion-exchange resin is embodied as the more substantially-sized forms such as described before. Alternatively, the cyclic amido-carbonyl cyano compound can be extracted from the liquid medium employed by using a suitable extraction solvent, and then it can be recovered from the extractant solution by evaporation, crystallization techniques or chromatographic methods, etc., if so desired.

Yields of the cyclic amido-carbonyl cyano compound can be high. Preferred practice within the spirit of this invention can provide yields of the cyclic amido-carbonyl cyano compound as great as at least about 50 percent of theory, at least as great as about 60 percent of theory, and at least as great as about 70 percent of theory.

Purity of the cyclic amido-carbonyl cyano compound product can be from good to excellent. The cyclic amidocarbonyl cyano compound prepared by the practice of this invention can have a high enough quality purity that the compound can be employed in its freshly prepared state as a reactant in further derivitizations. For example, N-alkylation, acylation, and acid salt formation steps can be carried out, and/or, derivitization of the cyano functionality can be carried out. Of course, if desired, the cyclic amido-carbonyl cyano compound can be itself further purified, to render it to be a very high or even ultra high purity compound, such as can be carried out by recrystallization techniques, chromatographic methods, and so forth.

The cyclization procedure of this invention is advantageously adapted to cyclization reactions where the otherwise reactable cyano moiety not desired to be reacted in general is left unreacted. For example, the cyano moiety, e.g., on an aromatic ring, otherwise able to undergo substantial hydrolysis and oxidation, e.g., to an aromatic carboxy moiety, which might otherwise react to form undesired by-product, can remain substantially inert to such a change during the cyclization practice of this invention, leaving the cyano moiety intact. And, this can occur with yields of such cyclic amido-carbonyl cyano compounds being yet high.

The following further illustrates this invention. Parts and percentages are by weight unless otherwise stated.

EXAMPLE 1

Preparation of racemic trans-3-(4-cyanophenyl)glycidic acid, methyl ester, was carried out as follows:

Preparation I

Into a 50 mL 3-neck, round-bottom flask fitted with a magnetic stirrer, 25 mL addition funnel, reflux condenser, and nitrogen adapter, was added 17 mL of anhydrous methanol via syringe. The flask contents were cooled in an ice bath, and to the cooled flask contents were added 1.1 g of sodium shot. A homogeneous mixture of 4.55 g (0.0419 mol) of methyl chloroacetate and 5.00 g (0.0381 mol) of 4-cyanobenzaldehyde in 20 mL of methanol was added dropwise, with stirring, to the cooled flask contents through the addition funnel over a period of 65 minutes. The flask and its contents were allowed to remain in the ice bath for about 30 minutes after addition was complete. To the thick mixture was then added about 10-15 mL of methanol, and stirring was continued for about 2 hours further. At that time, the flask contents were poured onto about 100 mL of ice; a sample of 1.0 mL of glacial acetic acid was added, and the mixture was stirred until the ice melted. Product solids, containing racemic trans-3-(4-cyanophenyl)glycidic acid, methyl ester, were collected by filtration, were rinsed well with room temperature water, and dried to yield 5.10 g of product (65.9 percent of theory). Proton nuclear magnetic resonance (HNMR) spectroscopy analysis was consistent with the proposed structure and this spectra looked clean. Thin layer chromatography (TLC) analysis (2:1 hexane, ethyl acetate) indicated some impurities.

A sample of 1.012 g of the above product solid was removed and recrystallized from 10 mL of reagent ethanol. A cold ethanol rinse was done, and the recrystallized product was dried to yield 0.83 g of recrystallized product (82.0 percent of theory for the recrystallization). Then the remainder of the 5.10 g of product above was recrystallized similarly from 40 mL of reagent ethanol, and this recrystallized product was isolated and dried to yield 3.33 g of recrystallized product (about 77 percent of theory for this recrystallization).

Preparation II

Into a 1 L 3-neck, round-bottom flask fitted with a magnetic stirrer, 250 mL addition funnel, reflux condenser, and nitrogen adapter, was added 150 mL of anhydrous methanol via syringe. The flask contents were cooled in an ice bath, and to the cooled flask contents were added 9.70 g of sodium shot. A homogeneous mixture of 32.5 mL (0.370 mol) of methyl chloroacetate and 44.00 g (0.336 mol) of 4-cyanobenzaldehyde in 175 mL of methanol, heating having been applied to dissolve the 4-cyanobenzaldehyde in the methanol, was added dropwise, with stirring, to the cooled flask contents through the addition funnel over a period of 2 hours. The flask and its contents were stirred in the ice bath for about 30 minutes after addition was complete and were then removed from the ice bath and stirred at ambient temperature for about 2½ hours, with the addition of 130 mL of methanol to the flask contents at 30 minutes from the beginning of the ambient temperature stirring. At that time, the flask contents were poured onto about 1 L of ice; a sample of 9.0 mL of glacial acetic acid was added, and the ice of the mixture was allowed to melt. Product solids, containing racemic trans-3-(4-cyanophenyl)glycidic acid, methyl ester, were collected by filtration, were rinsed with room temperature water, and dried to yield 64.48 g of product.

The entire sample of the above product solids was recrystallized from 650 mL of reagent ethanol. A cold ethanol rinse was done, and the recrystallized product was dried to yield 34.67 g of recrystallized product (50.8 percent of theory for this entire synthesis). The HNMR spectra was consistent with the proposed structure.

EXAMPLE 2

Preparation of racemic 2-hydroxy-3-(2-aminophenylthio) -3-(4-cyanophenyl)propionic acid, methyl ester, threo form, was carried out as follows:

Into a 300 mL round-bottom flask fitted with a magnetic stirrer, reflux condenser, thermometer and nitrogen adapter, was added 34.67 g (0.171 mol) of racemic trans-3-(4-cyanophenyl)-glycidic acid, methyl ester, from Example 1, and 175 mL of toluene. To this mixture was added 24.66 g (0.197 mol) of 2-aminothiophenol, and the resultant mixture was stirred and heated at reflux for nearly 10 hours as carried out by automatic timing. Stirring at ambient temperature was continued overnight.

No crystals had formed in the reaction mixture, and so, the mixture was cooled in an ice bath, cooled in a dry ice and acetone bath, whereupon some solid formed, and then returned to the ice bath, whereupon the solid redissolved fairly quickly. However, after a few minutes in the ice bath, massive crystallization occurred in the reaction vessel. The solid was collected and rinsed well with cold toluene to yield 40.78 g of product, which may not have been totally dry (nonetheless, estimated 72.6 percent of theory). The HNMR spectra of the product was consistent with the proposed structure, but there were some impurities present.

A sample of 1.219 g of the above product was removed and recrystallized from 5.0 mL of hot ethanol. The recrystallized solid was isolated and rinsed with cold ethanol, and then it was dried to yield 0.68 g (55.8 percent of theory for the recrystallization step). The HNMR spectra of the recrystallized product was consistent with the proposed structure.

The remainder of the same above product was recrystallized from 200 mL of hot ethanol. The recrystallized solid was isolated, retaining the mother liquor, and rinsed with cold ethanol, and then it was dried to yield 22.33 g of recrystallized product.

The mother liquor was concentrated to obtain 17.81 g of a yellow-colored oil, and the oil was crystallized from about 35 mL of hot ethanol. The crystallized solid was isolated and rinsed well with cold ethanol, and then it was dried to yield 5.99 g of crystallized product.

EXAMPLE 3

Cyclization of racemic 2-hydroxy-3-(2-aminophenylthio) -3-(4-cyanophenyl)propionic acid, methyl ester, threo form, into racemic cis-2-(4-cyanophenyl)-3-hydroxy-2,3-dihydro -1,5-abenzothiazepin-4(5H)-one was carried as follows:

Into a 100 mL round-bottom flask fitted with a magnetic stirrer, reflux condenser, and nitrogen adapter, was added a sample of racemic 2-hydroxy-3-(2-aminophenyl.thio)-3-(4-cyanophenyl)propionic acid, methyl ester, threo form (5.00 g, 0.0152 mol). To this was added 1.5 g of moist Dowex 50X4-400 ion-exchange resin, which previous to this had been soaked in 4 N HCl overnight and then washed with deionized water until the washings gave a neutral pH. Next was added 46 mL of water. The reaction vessel was lowered into an oil bath at about 120° C., and the mixture therein was stirred and refluxed initially. The oil bath temperature was lowered to about 95° C. for about an hour, whereupon it was then raised to about 110° C., and then to about 117° C. At about 12 hours after the oil bath was adjusted to about 117° C., heating and stirring were discontinued automatically. At about 8 hours after the heating and stirring were discontinued.

At this point another 1.0 g of moist Dowex 50X4-400 resin in its hydrogen ion form was added. This mixture was heated in the oil bath at about 120° C.

At about 21¾ hours after the latter heating started, the heating was stopped, and solid material was difficultly filtered from the mixture and rinsed with ether, ethyl acetate, and methanol to yield 4.44 g which was believed to probably contain residual Dowex resin. The HNMR of the solid indicated that the solid contained substantial amounts of the desired thiazepine product.

The solid was slurried in 100 mL of a 1:1 mixture of methanol and ethanol, and this mixture was heated, but dissolution was not completed. The mixture was filtered, retaining the filtrate, to yield 3.12 g of undried solids. These undried solids were slurried in 100 mL of acetone, and this mixture was heated at reflux. Solid was collected by filtration, saving the filtrate, and the collected solid was rinsed well with room temperature acetone to yield 1.12 g of solid, presumed to be mainly Dowex resin. The acetone, methanol, and ethanol filtrates were combined with the acetone rinsing, and this was evaporated to dryness to yield the desired thiazepine product (3.35 g, 74.4 percent yield of theory), confirmed by TLC analysis, which showed mainly one spot, which had migrated from the origin, with traces at the origin and also at a slightly more advanced migratory position on the TLC plate in relation to the desired thiazepine product.

EXAMPLE 4

N-Alkylation of racemic cis-2-(4-cyanophenyl)-3-hydroxy-2,3-dihydro-1,5-benzothiazepin-4(5H)-one into racemic cis-2-(4-cyanophenyl)-3-hydroxy-2,3-dihydro-5-[2-(N-piperidino)ethyl)]-1,5-benzothiazepin-4(5H)-one with hydrochloride salification was carried out as follows:

Into a 100 mL round-bottom flask, fitted with a magnetic stirrer, reflux condensor, and nitrogen adapter, was added 3.35 g of racemic cis-2-(4-cyanophenyl)-3-hydroxy-2,3-dihydro-1,5-benzothiazepin-4(5H)-one (0.0113 mol). To this was added 2.28 g of 1-(2-chloroethyl)piperidine hydrochloride (0.0124 mol) and 3.44 g of potassium carbonate (0.0249 mol). Then, 58 mL of ethyl acetate and 3.8 mL of water were added, and, with stirring under nitrogen, heating was carried out for 17¼ hours in an oil bath at 80° C. A replenishment of 50 mL more of ethyl acetate was added, and the reaction was continued for another 1¼ hours. Then, 1.9 mL of water and 0.22 g of 1-(2-chloroethyl)piperidine hydrochloride was added, and the reaction was continued with stirring and the heating for 4 hours more. The ethyl acetate layer was then washed with 3-25 mL portions of water, was dried over anhydrous sodium sulfate, and was concentrated to obtain 4.72 g of an oil.

Half of the oil was mixed with ether, and dry hydrogen chloride gas was passed therethrough. Solid was collected, washed well with ether, and dried to yield 2.24 g, which was recrystallized in 21 mL of a 15:6 mixture of ethanol to methanol, rinsed with ether, and dried to yield 1.54 g of the desired purified product salt. The HNMR spectroscopy was consistent with the proposed structure. Elemental analysis: Calculated: C, 62.22; H, 5.90; O, 7.21; N, 9.46; S, 7.22; Cl, 7.98. Found: C, 61.85, 61.89; H, 5.96, 5.97; N, 9.18, 9.23; S, 6.52, 6.39.

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A compound, or a pharmaceutically acceptable salt thereof, of the formula:

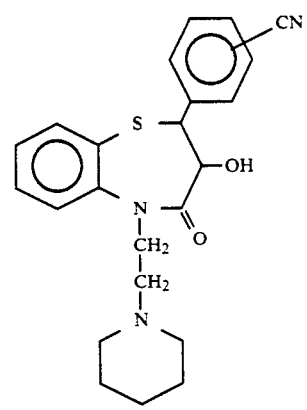

2. The compound of claim 1 which is cis-2-(4-cyanophenyl)-3-hydroxy-2,3-dihydro-5-[2-(N -piperidino)ethyl]-1,5-benzothiazepin-4(5H)-one hydrochloride (salt).

3. The compound of claim 2 which is (+)-cis-2-(4-cyanophenyl)-3-hydroxy-2,3-dihydro-5-[2-(N-piperidino)ethyl]-1,5-benzothiazepin-4(5H)-one hydrochloride (salt).

4. The compound of claim 2 which is (−)-cis-2-(4-cyanophenyl)-3-hydroxy-2,3-dihydro-5-[2-(N-piperidino)ethyl]-1,5-benzothiazepin-4(5H)-one hydrochloride (salt).

* * * * *